US009481874B2

(12) United States Patent
Fenel et al.

(10) Patent No.: US 9,481,874 B2
(45) Date of Patent: *Nov. 1, 2016

(54) METHOD TO IMPROVE THE STABILITY AND BROADEN THE PH RANGE OF FAMILY G/11 XYLANASES (71) Applicant: Danisco US Inc., Palo Alto, CA (US)

(72) Inventors: Fred Fenel, Helsinki (FI); Ossi Turunen, Vihti (FI); Matti Leisola, Espoo (FI)

(73) Assignee: DANISCO US INC.

( * ) Notice: Subject to any disclaimer, the term of this patent is extended or adjusted under 35 U.S.C. 154(b) by 66 days.

This patent is subject to a terminal disclaimer.

(21) Appl. No.: 14/488,124

(22) Filed: Sep. 16, 2014

(65) Prior Publication Data

US 2015/0011743 A1 Jan. 8, 2015

Related U.S. Application Data (60) Continuation of application No. 13/849,465, filed on Mar. 22, 2013, now Pat. No. 8,846,364, which is a division of application No. 11/963,285, filed on Dec. 21, 2007, now Pat. No. 8,426,181, which is a continuation of application No. 10/912,272, filed on Aug. 5, 2004, now Pat. No. 7,718,411, which is a continuation of application No. 10/110,079, filed as application No. PCT/FI00/00877 on Oct. 12, 2000, now abandoned.

(60) Provisional application No. 60/163,283, filed on Nov. 3, 1999.

(30) Foreign Application Priority Data

Oct. 12, 1999 (FI) ...................................... 19992186
Jul. 3, 2000 (FI) ...................................... 20001580

(51) Int. Cl.
  *C12N 9/24*    (2006.01)
  *C12N 9/42*    (2006.01)
  *C12P 19/04*   (2006.01)
  *C12N 1/20*    (2006.01)
  *C12N 15/00*   (2006.01)
  *C12N 15/74*   (2006.01)
  *C12P 21/06*   (2006.01)
  *C07H 21/04*   (2006.01)

(52) U.S. Cl.
  CPC ........... *C12N 9/2402* (2013.01); *C12N 9/2482* (2013.01); *C12Y 302/01008* (2013.01)

(58) Field of Classification Search
  None
  See application file for complete search history.

(56) References Cited

U.S. PATENT DOCUMENTS

| 5,405,769 | A | 4/1995 | Campbell et al. |
| 5,437,992 | A | 8/1995 | Bodie et al. |
| 5,736,384 | A | 4/1998 | Fukunaga et al. |
| 5,759,840 | A | 6/1998 | Sung et al. |
| 5,866,408 | A | 2/1999 | Sung et al. |
| 6,768,001 | B2 | 7/2004 | Saloheimo et al. |
| 8,426,181 | B2* | 4/2013 | Fenel ............ C12Y 302/01008 162/72 |

FOREIGN PATENT DOCUMENTS

| EP | 1 131 447 B1 | 9/2001 |
| WO | WO 95/34662 A1 | 12/1995 |
| WO | WO 97/27292 A1 | 7/1997 |
| WO | WO 97/36995 A2 | 10/1997 |
| WO | WO 00/29587 A1 | 5/2000 |

OTHER PUBLICATIONS

Arase, A. et al. "Stabilization of xylanase by random mutagenesis." *FEBS Letters* 316(2): 123-7, Jan. 25, 1993.
Bailey, M.J. et al. "Interlaboratory testing of methods for assay of xylanase activity." *Journal of Biotechnology* 23(3): 257-270, May 1992.
Biely, P. et al. "Soluble chromogenic substrates for the assay of endo-1,4-ß -xylanases and endo-1,4-ß -glucanases." *Analytical Biochemistry* 144(1): 142-146, Jan. 1985.
Davoodi, J. et al. "Scan-rate dependence in protein calorimetry: the reversible transitions of Bacillus circulans xylanase and a disulfide-bridge mutant." *Protein Science: A Publication of the Protein Society* 7(7): 1538-44, Jul. 1998.
Davoodi, J. et al. "Abnormally High pKa of an Active-Site Glutamic Acid Residue in Bacillus Circulans Xylanase." *European Journal of Biochemistry* 232(3): 839-843, 1995.
Fushinobu, S. et al. "Crystallographic and mutational analyses of an extremely acidophilic and acid-stable xylanase: biased distribution of acidic residues and importance of Asp37 for catalysis at low pH." *Protein Eng.* 11(12): 1121-1128, Dec. 1, 1998.
Georis, J. et al. "An additional aromatic interaction improves the thermostability and thermophilicity of a mesophilic family 11 xylanase: structural basis and molecular study." *Protein Sci* 9(3): 466-475, Mar. 1, 2000.
Gruber, K. et al. "Thermophilic Xylanase from Thermomyces lanuginosus: High-Resolution X-ray Structure and Modeling Studies." *Biochemistry* 37(39): 13475-13485, Sep. 29, 1998.
Harris, G.W. et al. "Structural basis of the properties of an industrially relevant thermophilic xylanase." *Proteins: Structure, Function, and Genetics* 29(1): 77-86, 1997.
Henrissat, B. et al. "New families in the classification of glycosyl hydrolases based on amino acid sequence similarities." *The Biochemical Journal* 293 ( Pt 3): 781-8, Aug. 1, 1993.

(Continued)

*Primary Examiner* — Iqbal H Chowdhury (57) ABSTRACT

The present invention relates to protein engineering, and concerns especially family G/11 xylanases, and genes encoding said enzymes. In specific, the invention concerns *Trichoderma reesei* XYNII gene, which codes for endo-1, 4-β-xylanase (EC 3.2.1.8). The invention describes how site-directed mutagenesis can be used to improve the properties of an enzyme to match the industrial conditions where it is used. Protein engineering can be used to improve thermoactivity and thermostability of xylanases, as well as to broaden their pH range.

7 Claims, 5 Drawing Sheets

(56) References Cited

OTHER PUBLICATIONS

Lawson, S.L. et al. "Positioning the acid/base catalyst in a glycosidase: studies with Bacillus circulans xylanase." *Biochemistry* 36(8): 2257-65, Feb. 25, 1997.

Lawson, S.L. et al. "Effects of both Shortening and Lengthening the Active Site Nucleophile of Bacillus circulans Xylanase on Catalytic Activity." *Biochemistry* 35(31): 10110-10118, Aug. 6, 1996.

Moreau, A. et al. "Increase in catalytic activity and thermostability of the xylanase A of Streptomyces lividans 1326 by site-specific mutagenesis." *Enzyme and Microbial Technology* 16(5): 420-4, May 1994.

Prade, R.A. "Xylanases: from biology to biotechnology." *Biotechnology & Genetic Engineering Reviews* 13: 101-31, 1996.

Sung, W.L. et al. "Expression of Trichoderma reesei and Trichoderma viride xylanases in *Escherichia coli*." *Biochemistry and Cell Biology* 73(5-6): 253-9, Jun. 1995.

Tenkanen, M. et al. "Two major xylanases of Trichoderma reesei." *Enzyme and Microbial Technology* 14(7): 566-574, 1992.

Törrönen, A. et al. "Structural and functional properties of low molecular weight endo-1,4-ß -xylanases." *Journal of Biotechnology* 57(1): 137-149, Sep. 16, 1997.

Torronen, A. et al. "Structural comparison of two major endo-1,4-xylanases from Trichoderma reesei." *Biochemistry* 34(3): 847-56, Jan. 24, 1995.

Vogt, G. et al. "Protein thermal stability, hydrogen bonds, and ion pairs." *Journal of Molecular Biology* 269(4): 631-643, Jun. 20, 1997.

Wakarchuk, W.W. et al. "Thermostabilization of the Bacillus circulansxylanase by the introduction of disulfide bonds." *Protein Eng.* 7(11): 1379-1386, Nov. 1, 1994.

* cited by examiner

| | |
|---|---|
| T2C | 5'-GAGAAGCGCCAGTGCATTCAGCCCGGC-3' |
| T28C | 5'-GTGACGTACTGCAATGGTCCCGGCGGG-3' |
| K58R | 5'-GGCACCAAGAACAGGGTCATCAACTTCTCGGGC-3' |
| I91D | 5'-TCCATCACCGTCAGCGATTAAAGGGGGCTCTTC-3' |
| P5C | 5'-CCCAGACGATTCAGTGCGGCACGGGCTACAAC-3' |
| N19C | 5'-CTTCTACTCGTACTGGTGCGATGGCCACGGCG-3' |
| T7C | 5'-CGATTCAGCCCGGCTGCGGCTACAACAACGGC-3' |
| S16C | 5'-CAACGGCTACTTCTACTGCTACTGGAACGATGGCC-3' |
| N10C | 5'-CCGGCACGGGCTACTGCAACGGCTACTTCTACTC-3' |
| N29C | 5'-GGCGTGACGTACACCTGCGGTCCCGGCGGGC-3' |
| L105C | 5'-GGCGCCACCAAGTGCGGCGAGGTCACC-3' |
| Q162C | 5'-GCGTGGGCTCAGTGCGGCCTGACGCTCG-3' |

METHOD TO IMPROVE THE STABILITY AND BROADEN THE PH RANGE OF FAMILY G/11 XYLANASES

CROSS REFERENCE TO RELATED APPLICATIONS

This application is a Continuation of U.S. patent application Ser. No. 13/849,465, filed Mar. 22, 2013, which is a divisional of U.S. patent application Ser. No. 11/963,285, filed Dec. 21, 2007 (now U.S. Pat. No. 8,426,181), which is a Continuation of U.S. patent application Ser. No. 10/912,272, filed Aug. 5, 2004 (now U.S. Pat. No. 7,718,411), which is a Continuation of U.S. patent application Ser. No. 10/110,079, filed Apr. 29, 2002, abandoned, which is a National Phase under 37 CFR 371 of International application PCT/FI00/00877, filed Oct. 12, 2000, which claims priority to U.S. provisional application 60/163,283, filed Nov. 3, 1999, the contents of all of the above are incorporated by reference in their entirety.

SEQUENCE LISTING

The sequence listing submitted via EFS, in compliance with C.F.R. §1.52(e), is incorporated herein by reference. The sequence listing text file submitted via EFS contains the file "30760-US-CNT-3_SeqListing.txt", created on Sep. 16, 2014, which is 4.79 KB (4,906 bytes) in size.

FIELD OF THE INVENTION

This invention relates to protein engineering, and concerns especially family G/11 xylanases, and genes encoding said enzymes. In specific, the invention concerns *Trichoderma reesei* XYNII gene, which codes for endo-1,4-β-xylanase (EC 3.2.1.8). The invention describes how site-directed mutagenesis can be used to improve the properties of an enzyme to match the industrial conditions where it is used. Protein engineering can be used to improve thermoactivity and thermostability of xylanases, as well as to broaden their pH range.

BACKGROUND OF THE INVENTION

Xylanases are glycosyl hydrolases which hydrolyse β-1,4-linked xylopyranoside chains. Xylanases have been found in at least a hundred different organisms. Together with other glycosyl hydrolases they form a superfamily which includes more than 40 different enzyme families (Henrissat and Bairoch, 1993). Family 11 (previously G) xylanases are defined by the similarities in their gene sequences, protein structures, and catalytic mechanisms. Common features for the members of this family are high genetic homology, a size of about 20 kDa, and a double displacement catalytic mechanism (Tenkanen et al., 1992; Wakarchuk et al., 1994).

The family 11 xylanases mainly consist of β-strands which form two large β-sheets, and of one α-helix. These form a structure that resembles a partly-closed right hand, wherein the β-sheets are called A- and B-sheet. (Törrönen & Rouvinen, 1997). The family 11 xylanases have special interest in industrial applications, because their structure is stable, and they are not susceptible to protease activity. In addition, xylanases can be produced economically on an industrial scale. *Trichoderma reesei* is known to produce three different xylanases of which xylanases I and II (XynI and XynII) are the best characterized (Tenkanen et al., 1992). XynI has a size of 19 kDa, and compared to XynII it has low isoelectric point and pH optimum (pI 5.5, pH 3-4). XynII has a size of 20 kDa and it has a pI of 9.0 and a pH optimum of 5.0-5.5 (Törrönen and Rouvinen, 1995).

The most important industrial applications of xylanases are pulp bleaching, modification of textile fibres, and biomass modification to improve its digestion in animal feeding (Prade, 1996). A common nominator in all these applications is the extreme conditions which face the enzyme. High temperatures, and pH which substantially differs from the optimal pH of many xylanases decrease the effective utility of the presently available xylanases in industrial applications.

In feed applications the enzyme faces high temperature conditions for a short time (e.g. 2-5 min at 90° C.) during feed preparation. However, the actual catalytic activity of the enzyme is needed at lower temperatures (e.g. ~37° C.). Consequently, the enzyme should not be inactivated irreversibly at high temperatures, while it has to be active at relatively low temperatures.

In pulp bleaching the material coming from alkaline wash has a high temperature (>80° C.) and pH (>10). None of the commercially available xylanases survives these conditions. The pulp must be cooled and the alkaline pH neutralized in order to treat the pulp with presently available xylanases. This means increased costs. Protein engineering has been used—sometimes successively—to stabilise xylanases to resist the denaturing effect of the high temperature and pH.

Several thermostable, alkaliphilic and acidophilic xylanases have been found and cloned from thermophilic organisms (Bodie et al., 1995; Fukunaga et al., 1998). However, production of economical quantities of these enzymes has in most cases proved to be difficult. Therefore the *T. reesei* xylanase II, which is not as such thermostable, is in industrial use because it can be produced at low cost in large quantities. As an alternative for isolating new xylanases, or developing production processes, one can envisage engineering the presently used xylanases to be more stable in extreme conditions.

The stability of *Bacillus circulans* xylanase has been improved by disulfide bridges, by binding the N-terminus of the protein to the C-terminus and the N-terminal part of the α-helix to the neighbouring β-strand (Wakarchuk et al., 1994). Also Campbell et al. (1995) have modified *Bacillus circulans* xylanase by inter- and intramolecular disulfide bonds in order to increase thermostability. On the other hand, the stability of *T. reesei* xylanase II has been improved by changing the N-terminal region to a respective part of a thermophilic xylanase (Sung et al., 1998). In addition to the improved thermostability, the activity range of the enzyme was broadened in alkaline pH. Single point mutations have also been used to increase the stability of *Bacillus pumilus* xylanase (Arase et al., 1993). The influence of mutagenesis on stability has been studied on many other enzymes. By comparing the structures of thermophilic and mesophilic enzymes plenty of information has been obtained (Vogt et al., 1997). Structural information of thermophilic xylanases has also given information about factors influencing the thermostability of xylanases (Gruber et al., 1998; Harris et al., 1997).

SUMMARY OF THE INVENTION

The present invention relates to xylanases which belong to the family 11(previously G) glycosyl hydrolases. The invention provides xylanases modified so as to change their thermostability, thermoactivity, and/or broaden their pH range.

Various modifications in the *Trichoderma reesei* xylanase structure, either alone or in combinations, result in the changes described in this invention:

(1) the stability of the enzyme is increased by binding of the N-terminal region by disulfide bridges (for example, the bridges formed by the mutation pairs T2C and T28C; P5C and N19C; T7C and S16C; N10C and N29C) to the body of the protein;

(2) the C-terminus is stabilised by extension with additional aspartic acid (+191D) which forms a salt bridge with arginine 58 (lysine 58 in the wild-type enzyme has been changed to arginine (K58R));

(3) the stability of the enzyme is increased by binding the a-helix by a disulfide bridge to the body of the enzyme (e.g. L105C and Q162C);

(4) point mutations have been made at different positions to improve the stability of xylanase (N11D, T26R, G30H, N67R, N97R, A132R, N157R, A160R, T165N, M169H, S186R).

In specific, the present invention provides a modified *Trichoderma reesei* xylanase in which the amino acids T2 and T28 have been changed to cysteines, K58 has been changed to arginine, and to the C-terminus of the enzyme an aspartic acid has been added (+191D), thereby forming a disulfide bridge between the amino acids T2C and T28C, and a salt bridge between the amino acids K58R and +191D.

BRIEF DESCRIPTION OF DRAWINGS

FIG. 1. A set of oligonucleotides used in the mutagenesis of xylanase (codon changes underlined). The sequences are also given in the appended Sequence Listing as sequences 1 to 12. More specifically, the oligonucleotides correspond to the sequences in the sequence listing as follows: T2C is SEQ ID NO:1, T28C is SEQ ID NO:2, K58R is SEQ ID NO:3, 191D is SEQ ID NO:4, P5C is SEQ ID NO:5, N19C is SEQ ID NO:6, T7C is SEQ ID NO:7, S16C is SEQ ID NO:8, N10C is SEQ ID NO:9, N29C is SEQ ID NO:10, L105C is SEQ ID NO:11, and Q162C is SEQ ID NO:12.

DETAILED DESCRIPTION OF THE INVENTION

The family G/11 xylanases originating from bacteria, yeast and fungi have common molecular structure. Examples of such xylanases are:
*Aspergillus niger* XynA
*Aspergillus kawachii* XynC
*Aspergillus tubigensis* XynA
*Bacillus circulans* XynA
*Bacillus pumilus* XynA
*Bacillus subtilis* XynA
*Neocallimastix patriciarum* XynA
*Streptomyces lividans* XynB
*Streptomyces lividans* XynC
*Streptomyces thermoviolaceus* XynII
*Thermomonospora fusca* XynA
*Trichoderma harzianum* Xyn
*Trichoderma reesei* XynI, *Trichoderma reesei* XynII
*Trichoderma viride* Xyn The invention deals with xylanases of the family G/11 with the following common features:

Enzymes in which the N-terminal sequence is a part of the double-layered β-sheet (in the family 11 xylanases the A- and the B-sheet, (Gruber, et al., 1998)) and in which the first β-strand (in *T. reesei* XynII the amino acids 5-10) or the N-terminal end can be bound by disulfide bridges either to the adjacent β-strands (in *T. reesei* XynII the amino acids 13-19) or to other neighbouring regions.

(ii). Enzymes in which the C-terminal peptide chain forms a β-strand (in *T. reesei* XynII amino acids 183-190), which is a part of a larger β-sheet and in which the C-terminal region can be bound by disulfide bridges to the adjacent β-strands or by salt bridges to the body of the enzyme.

(iii). Enzymes which have an α-helix on the other side of the enzyme structure with regard to the catalytic canyon, and wherein said α-helix or the neighbouring regions can be bound more tightly by a disulfide bridge to the body of the protein.

The *T. reesei* xylanase II has the above mentioned properties and in said enzyme thermostability, pH-stability and thermoactivity can be modified based on these properties. The following changes have been made to the xylanase gene (XYNII) of *T. reesei:*

By site-directed mutagenesis disulfide bridges are formed in the N-terminal region:

Threonines 2 and 28 are changed to cysteines resulting in a disulfide bridge being formed between them (T2C and T28C).

Proline 5 and asparagine 19 are changed to cysteines resulting in a disulfide bridge being formed between them (P5C and N19C).

Threonine 7 and serine 16 are changed to cysteines resulting in a disulfide bridge being formed between them (T7C and S16C).

Asparagine 10 and asparagine 29 are changed to cysteines resulting in a disulfide bridge being formed between them (N10C and N29C).

By site-directed mutagenesis, the C-terminus is bound more tightly to the body of the enzyme by adding as a recombinant change one amino acid (e.g. aspartic acid or glutamic acid) to the C-terminus of the xylanase, which then forms a salt bridge from the C-terminus to the body of the enzyme. If appropriate, a suitable amino acid replacement can be made in the body of the protein, so as to enable the formation of a salt bridge.

An aspartic acid (+191D) is added to the C-terminal serine (S190). This results in a salt bridge with arginine at position 58, where wild-type lysine has been replaced by arginine (K58R).

By site-directed mutagenesis at least one disulfide bridge is formed to stabilise the enzyme in the C-terminal part via the α-helix or a region near the α-helix.

Leucine 105 and glutamine 162 are changed to cysteines resulting in disulfide bridge between them (L105C and Q162C).

By site-directed mutagenesis point mutations are made to increase the stability of *T. reesei* xylanase II: N11D, T26R, G30H, N67R, N97R, A132R, N157R, A160R, T165N, M169H, S186R.

Methods of the Invention

Production of mutated and recombinant XYNII genes were carried out by the following general procedures:

Expression Vector and Production of the Enzyme

*T. reesei* xylanase II was produced in *E. coli* strains XL1-Blue or Rv308 using the vector pKKtac (VTT, Espoo, Finland) or the vector pALK143 (ROAL, Rajamäki, Finland) *T. reesei* XYNII gene was directly cloned by PCR from the cDNA of *T. reesei* to the vector pKKtac (induction of expression by IPTG). Alternatively, the plasmid pALK143 was used which contains *T. reesei* XYNII gene. Both of the vectors secrete the xylanase into the medium; the vector pKKtac by pectate lyase (pelB) signal sequence and the vector pALK143 by amylase signal sequence.

2. Site-Directed Mutagenesis and Production of Recombinant XYNII Gene

Figure 1:
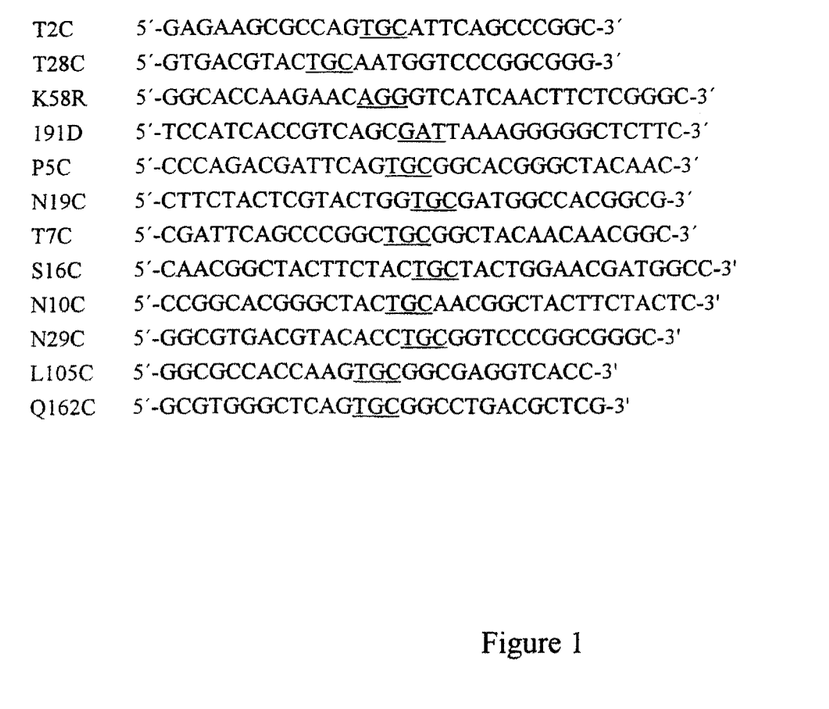

The production of mutated *T. reesei* XYNII gene used in the Examples of this application, was effected as follows: Mutations were produced by polymerase chain reaction (PCR) using oligonucleotide primers which contained the sequences for the changed codons. Examples of the used oligonucleotides are given in FIG. 1, as well as in the appended Sequence Listing as sequences 1 to 12. PCR using the primers (containing the desired mutation) was carried out by Quick Change method (Stratagene, Westburg, Leusden, The Netherlands) and by generally known methods. PfuTurbo was used as DNA polymerase (Stratagene, La Jolla, Calif., USA). The cloned *E. coli* strains were cultivated on plates containing xylan (birchwood xylan: Sigma, Steinheim, Germany) coupled to Rhemazol Brilliant Blue. The xylanase activity could be seen as halos around the colonies (Biely et al., 1985).

3. Determination of the Activity of Xylanases

The xylanase activity of enzyme samples was determined by measuring the amount of reducing sugars released from the hydrolysed xylan fibre. The reducing sugars were measured by DNS-method in 50 mM citrate-phosphate buffer (Bailey et al., 1992). Standard activity determination was carried out at pH 5 and 50° C.

4. Determination of the Stability of the Enzymes

The stability of the xylanases was tested by measuring the half-life of the modified enzymes at different temperatures. The enzyme was incubated for varying times at 55 or 65° C. and the residual activity was measured as described above. The stability at high temperatures was also measured by incubating the enzymes for 10 min at varying temperatures and subsequently measuring the residual activity by DNS-method. The pH-dependent xylanase activity was measured by determining the enzyme activity in varying pH-values. The temperature optimum of the enzyme was determined by measuring the activity at varying temperatures (10 min, pH 5). The properties of the mutated enzymes were compared to the wild-type *T. reesei* XynII enzyme.

EXAMPLES OF MUTATIONS

Example 1

Figure 2:
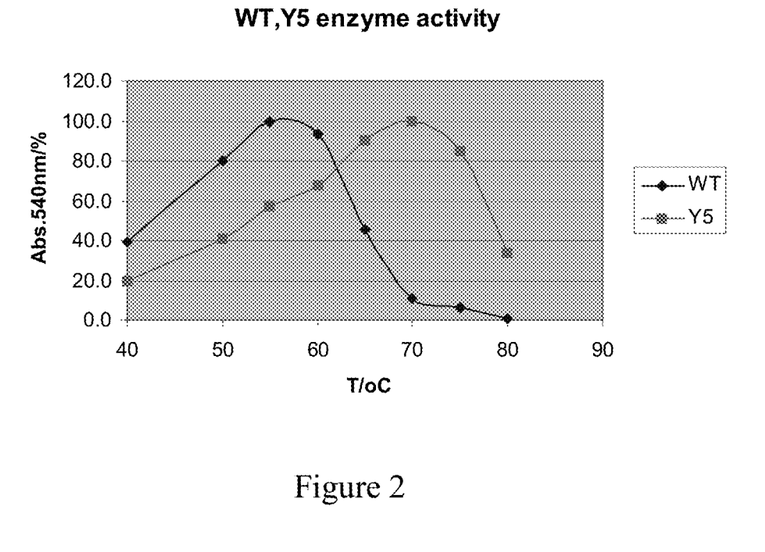
FIG. 2. A graph presenting the effect of the mutations T2C, T28C, K58R, and +191D on the thermal optimum of *T. reesei* XynII (WT=wild-type enzyme; Y5=the mutated *T. reesei* XynII).

The three-fold mutations (T2C, T28C and K58R) and the recombinant change (+191D) were made in *T. reesei* XynII by using the methods described above. The mutant enzyme was designated as Y5. Said mutant enzyme was expressed in *E. coli*, which was cultivated at +37° C. in shake flasks using Luria Broth as growth medium. After cultivation the cells were removed by centrifugation and the xylanase secreted into the medium was characterized in varying conditions, as described above. FIG. 2 shows the effect of the temperature to the enzyme activity when the mutant Y5 (T2C, T28C, K58R, +191D) and the wild-type (*T. reesei* XynII) enzyme were incubated for 10 min with birchwood xylan in varying temperatures, and the relative amount of the reducing sugars as released were measured with DNS-method. Said mutations improved the temperature optimum of xylanase by about 15° C.

Example 2

Figure 3:
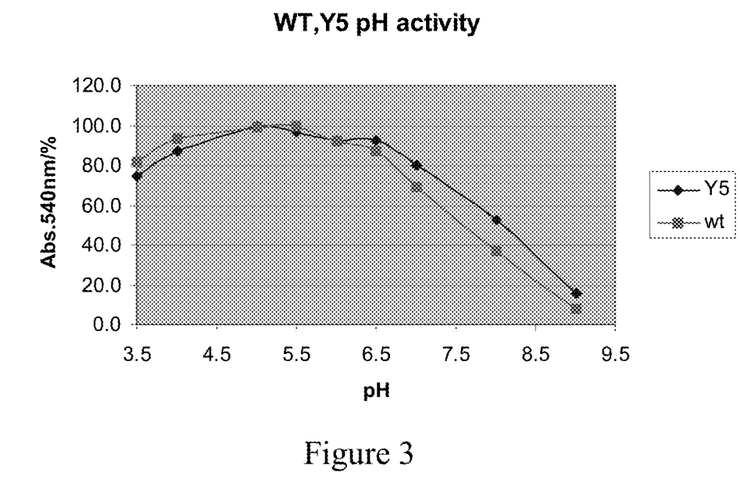
FIG. 3. A graph presenting the effect of the mutations T2C, T28C, K58R, and +191D on the pH-dependent activity of *T. reesei* XynII (WT and Y5 as in FIG. 2).

The three-fold mutant xylanase (T2C, T28C, K58R, +191D) described in Example 1 was incubated for 10 min in 1% birchwood xylan at 50° C. in citrate-phosphate buffer in varying pH-values. FIG. 3 shows the relative amount of reducing sugars as released for the mutant and the wild-type xylanases. The mutations broadened slightly the pH-dependent activity of the enzyme to alkaline direction. The mutant enzyme was more active than the wild-type enzyme at pH 7-8; the activity of mutant enzyme was about 20% higher at pH 8 (50° C.).

Example 3

Figure 4:
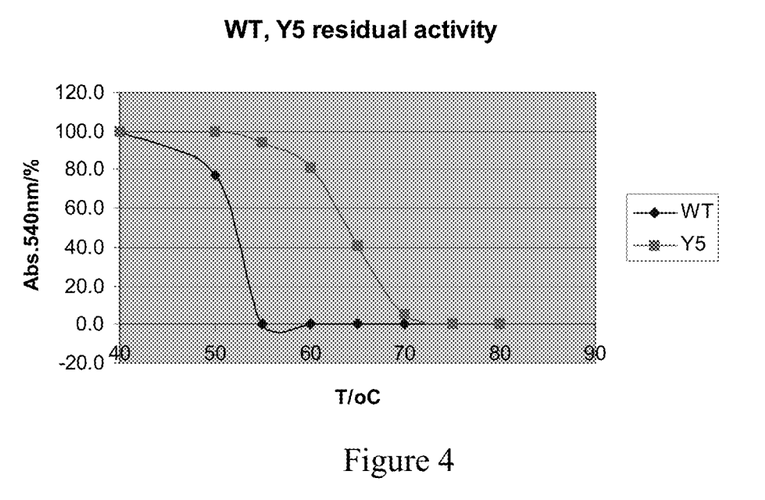
FIG. 4. A graph presenting the effect of the mutations T2C, T28C, K58R, and +191D on the inactivation of *T. reesei* XynII at different temperatures (WT and Y5 as in FIG. 2).

The above-mentioned three-fold mutant (T2C, T28C, K58R,+191D) and the wild-type enzyme were incubated for 10 min at varying temperatures. After the incubation the samples were cooled and the residual activity was determined in standard conditions. The wild-type enzyme was completely inactivated already at 55-60° C. The mutant enzyme retained about 50% of its activity even at 65 ° C. (FIG. 4). Table 1 below shows the half-lives (T½) of the mutant (Y5) and the wild-type xylanase at 55° C. and 65° C.

TABLE 1

|  | pH 5 | pH 8 |
|---|---|---|
| 55° C. | | |
| Y5 | stable | stable |
| Wild-type XynII | ~5 min | ~2 min |
| 65° C. | | |
| Y5 | 20-25 min | ~10 min |
| Wild-type XynII | 40 sec | |

Example 4

Figure 5:
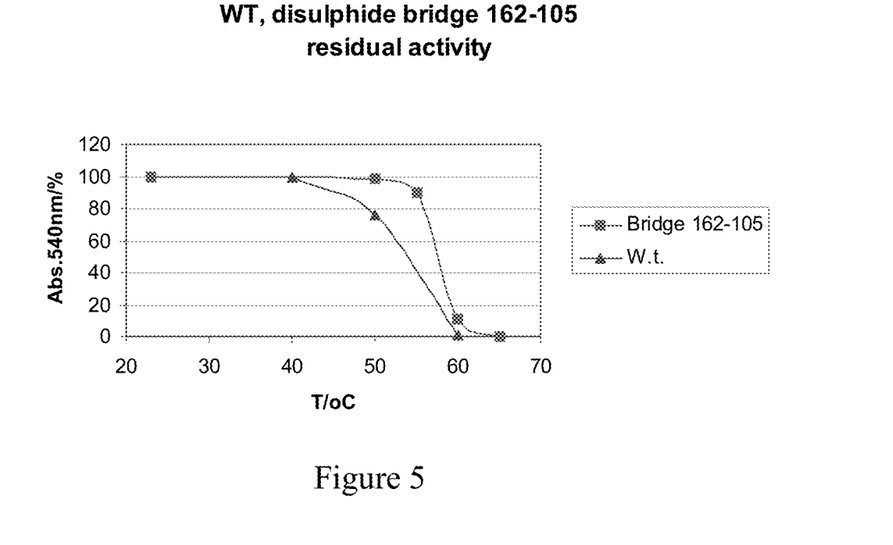
FIG. 5. A graph presenting the effect of the mutations Q162C and L105C on the inactivation of *T. reesei* XynII at different temperatures (W.t.=wild-type enzyme).

With the above-mentioned methods a disulfide bridge was made (L105C and Q162C) to bind the C-terminus of the α-helix to the neighbouring β-strand. The enzyme was produced in *E. coli* and its properties were determined FIG. 5 shows the inactivation of the mutant enzyme at different temperatures compared to the wild-type enzyme. At 55° C. the stability of the mutated enzyme increased about 20-fold, with regard to the wild-type enzyme, whereby the half-life increased from 5 min (the wild-type enzyme) up to about 1,5 hours (the mutated enzyme).

Literature

Arase, A., Yomo, T., Urabe, I., Hata, Y., Katsube, Y. & Okada, H. (1993). Stabilization of xylanase by random mutagenesis. *FEBS Letters* 316, 123-7.

Bailey, J. M., Biely, P. & Poutanen, K. (1992). Interlaboratory testing of methods for assay of xylanase activity. *J. Biotech.* 23, 257-270.

Biely, P., Mislovicova, D. & Toman, R. (1985). Soluble chromogenic substrates for the assay of endo-1,4-beta-xylanases and endo-1,4-beta-glucanases. *Analytical Biochemistry* 144, 142-6.

Bodie, E., Cuevas, W. A. & Koljonen, M. (1995). In U.S. Pat. No. 5,437,992.

Campbell, R. L., Rose, D. R., Sung, W. L., Yaguchi, M. & Wakarchuck, W. (1995). In U.S. Pat. No. 5,405,769.

Fukunaga, N., Iwasaki, Y., Kono, S., Kita, Y. & Izumi, Y. (1998). In U.S. Pat. No. 5,736,384.

Gruber, K., Klintschar, G., Hayn, M., Schlacher, A., Steiner, W. & Kratky, C. (1998). Thermophilic xylanase from Thermomyces lanuginosus: High-resolution X-ray structure and modeling studies. *Biochemistry* 37, 13475-13485.

Harris, G. W., Pickersgill, R. W., Connerton, I., Debeire, P., Touzel, J. P., Breton, C. & Perez, S. (1997). Structural basis of the properties of an industrially relevant thermophilic xylanase. *Proteins* 29, 77-86.

Henrissat, B. & Bairoch, A. (1993). New families in the classification of glycosyl hydrolases based on amino acid sequence similarities. *Biochemical Journal* 293, 781-8.

Prade, R. A. (1996). Xylanases: from biology to biotechnology. *Biotechnology & Genetic Engineering Reviews* 13, 101-31.

Sung, W. L., Yaguchi, M., Ishikawa, K., Huang, F., Wood, M. & Zahab, D. M. (1998). In U.S. Pat. No. 5,759,840.

Tenkanen, M., Puls, J. & Poutanen, K. (1992). Two major Xylanases of Trichoderma reesei. *Enzyme Microb. Technol.* 14, 566-574.

Törrönen, A. & Rouvinen, J. (1995). Structural comparison of two major endo-1,4-xylanases from Trichoderma reesei. *Biochemistry* 34, 847-56.

Törrönen, A. & Rouvinen, J. (1997). Structural and functional properties of low molecular weight endo-1,4-beta-xylanases. *Journal of Biotechnology* 57, 137-49.

Wakarchuk, W. W., Sung, W. L., Campbell, R. L., Cunningham, A., Watson, D. C. & Yaguchi, M. (1994). Thermostabilization of the Bacillus circulans xylanase by the introduction of disulfide bonds. *Protein Engineering* 7, 1379-86.

Vogt, G., Woell, S. & Argos, P. (1997). Protein thermal stability, hydrogen bonds, and ion pairs. *Journal of Molecular Biology* 269, 631-43.

The invention claimed is:

1. A recombinant gene encoding a variant xylanase having increased thermo stability or pH-stability when compared to a corresponding wild-type enzyme, wherein said variant comprises at least 95% sequence identity over the full length amino acid sequence of SEQ ID NO: 13, said variant having amino acid substitutions at positions corresponding to amino acids 2 and 28 of SEQ ID NO: 13.

2. The recombinant gene according to claim 1, wherein said variant has a cysteine at positions 2 and 28.

3. The recombinant gene according to claim 2, further comprising an arginine at amino acid position 58 and an aspartic acid residue (+191D) at the C-terminus of the enzyme.

4. The recombinant gene according to claim 3, wherein the wild-type enzyme has the amino acid sequence of SEQ ID NO:13.

5. The recombinant gene of claim 3, comprising SEQ ID NO:13 modified to have T2C, T28C, K58R, and +191D amino acids.

6. A recombinant gene encoding a variant xylanase having increased thermostability or pH-stability when compared to corresponding wild-type enzyme, wherein said variant comprises at least a 95% sequence identity over the full length amino acid sequence of SEQ ID NO:13, said variant further comprising an aspartic acid (+191D) at the C terminus.

7. The recombinant gene according to claim 6, wherein said variant has an arginine at a position corresponding to position 58 of SEQ ID NO:13.

* * * * *

```
                         SEQUENCE LISTING

<160> NUMBER OF SEQ ID NOS: 13

<210> SEQ ID NO 1
<211> LENGTH: 27
<212> TYPE: DNA
<213> ORGANISM: Artificial Sequence
<220> FEATURE:
<223> OTHER INFORMATION: synthetic oligonucleotide used in the mutation
      T2C

<400> SEQUENCE: 1
gagaagcgcc agtgcattca gcccggc                                          27

<210> SEQ ID NO 2
<211> LENGTH: 27
<212> TYPE: DNA
<213> ORGANISM: Artificial Sequence
<220> FEATURE:
<223> OTHER INFORMATION: synthetic oligonucleotide used in the mutation
      T28C

<400> SEQUENCE: 2
gtgacgtact gcaatggtcc cggcggg                                          27

<210> SEQ ID NO 3
<211> LENGTH: 33
<212> TYPE: DNA
<213> ORGANISM: Artificial Sequence
<220> FEATURE:
<223> OTHER INFORMATION: synthetic oligonucleotide used in the mutation
      K58R

<400> SEQUENCE: 3
ggcaccaaga acagggtcat caacttctcg ggc                                   33

<210> SEQ ID NO 4
<211> LENGTH: 33
<212> TYPE: DNA
<213> ORGANISM: Artificial Sequence
<220> FEATURE:
<223> OTHER INFORMATION: synthetic oligonucleotide used in the mutation
      +191D

<400> SEQUENCE: 4
tccatcaccg tcagcgatta aaggggggctc ttc                                  33
```

<210> SEQ ID NO 5
<211> LENGTH: 32
<212> TYPE: DNA
<213> ORGANISM: Artificial Sequence
<220> FEATURE:
<223> OTHER INFORMATION: synthetic oligonucleotide used in the mutation
      P5C

<400> SEQUENCE: 5
cccagacgat tcagtgcggc acgggctaca ac                                  32

<210> SEQ ID NO 6
<211> LENGTH: 32
<212> TYPE: DNA
<213> ORGANISM: Artificial Sequence
<220> FEATURE:
<223> OTHER INFORMATION: synthetic oligonucleotide used in the mutation
      N19C

<400> SEQUENCE: 6
cttctactcg tactggtgcg atggccacgg cg                                  32

<210> SEQ ID NO 7
<211> LENGTH: 32
<212> TYPE: DNA
<213> ORGANISM: Artificial Sequence
<220> FEATURE:
<223> OTHER INFORMATION: synthetic oligonucleotide used in the mutation
      T7C

<400> SEQUENCE: 7
cgattcagcc cggctgcggc tacaacaacg gc                                  32

<210> SEQ ID NO 8
<211> LENGTH: 35
<212> TYPE: DNA
<213> ORGANISM: Artificial Sequence
<220> FEATURE:
<223> OTHER INFORMATION: synthetic oligonucleotide used in the mutation
      S16C

<400> SEQUENCE: 8
caacggctac ttctactgct actggaacga tggcc                               35

<210> SEQ ID NO 9
<211> LENGTH: 34
<212> TYPE: DNA
<213> ORGANISM: Artificial Sequence
<220> FEATURE:
<223> OTHER INFORMATION: synthetic oligonucleotide used in the mutation
      N10C

<400> SEQUENCE: 9
ccggcacggg ctactgcaac ggctacttct actc                                34

<210> SEQ ID NO 10
<211> LENGTH: 31
<212> TYPE: DNA
<213> ORGANISM: Artificial Sequence
<220> FEATURE:
<223> OTHER INFORMATION: synthetic oligonucleotide used in the mutation
      N29C

<400> SEQUENCE: 10
ggcgtgacgt acacctgcgg tcccggcggg c                                   31

<210> SEQ ID NO 11
<211> LENGTH: 27
<212> TYPE: DNA
<213> ORGANISM: Artificial Sequence
<220> FEATURE:
<223> OTHER INFORMATION: synthetic oligonucleotide used in the mutation L105C

<400> SEQUENCE: 11
ggcgccacca agtgcggcga ggtcacc    27

<210> SEQ ID NO 12
<211> LENGTH: 28
<212> TYPE: DNA
<213> ORGANISM: Artificial Sequence
<220> FEATURE:
<223> OTHER INFORMATION: synthetic oligonucleotide used in the mutation Q162C

<400> SEQUENCE: 12
gcgtgggctc agtgcggcct gacgctcg    28

<210> SEQ ID NO 13
<211> LENGTH: 190
<212> TYPE: PRT
<213> ORGANISM: Trichoderma reesei

<400> SEQUENCE: 13

```
Gln Thr Ile Gln Pro Gly Thr Gly Tyr Asn Asn Gly Tyr Phe Tyr Ser
 1               5                  10                  15

Tyr Trp Asn Asp Gly His Gly Gly Val Thr Tyr Thr Asn Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
        50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```